United States Patent

Baldwin et al.

[11] Patent Number: 5,177,468
[45] Date of Patent: Jan. 5, 1993

[54] CONDUIT LINER MONITOR

[75] Inventors: Stanley L. Baldwin; Payam Towfigh, both of Winnipeg; Stuart E. Street, Thompson, all of Canada

[73] Assignee: Inco Limited, Toronto, Canada

[21] Appl. No.: 801,281

[22] Filed: Dec. 2, 1991

[30] Foreign Application Priority Data

Mar. 20, 1991 [CA] Canada ................................. 2038701

[51] Int. Cl.⁵ ............................................. G08B 21/00
[52] U.S. Cl. .................................... 340/652; 137/551; 137/552; 340/540; 340/605
[58] Field of Search ...................... 340/605, 540, 652; 137/551, 552

[56] References Cited

U.S. PATENT DOCUMENTS

| | | | |
|---|---|---|---|
| 1,962,168 | 6/1934 | Andrus | 340/605 |
| 2,759,175 | 8/1956 | Spalding | 340/605 |
| 3,375,702 | 4/1968 | Birman | 340/605 |
| 3,874,222 | 4/1975 | Ladd et al. | 340/524 |
| 4,107,672 | 8/1978 | Van Riemsdijk et al. | 340/605 |
| 4,404,516 | 9/1983 | Johnson, Jr. | 324/557 |
| 4,446,892 | 5/1984 | Maxwell | 138/104 |

FOREIGN PATENT DOCUMENTS

| | | | |
|---|---|---|---|
| 0185650 | 6/1986 | European Pat. Off. | 11/12 |
| 2023296 | 12/1979 | United Kingdom . | |
| 2148447 | 5/1985 | United Kingdom . | |

Primary Examiner—Glen R. Swann, III
Attorney, Agent, or Firm—E. A. Steen; B. T. Biederman

[57] ABSTRACT

The monitor allows for the non-destructive determination of the status of a liner disposed within a conduit. The conduit may, for example, be an elbow, valve, pipe. At least one wire is disposed within the liner in an area of concern. The wire is connected to a receptacle located on the conduit. A status display plugs into the receptacle and checks the continuity of the wire. If a wire is broken, this information is displayed, indicating a potential problem with the liner.

8 Claims, 3 Drawing Sheets

CONDUIT LINER MONITOR

TECHNICAL FIELD

The instant invention relates to piping systems in general and, more particularly, to a monitor for sensing the deterioration of protective liners disposed within conduits.

BACKGROUND ART

Erosive materials flowingly transported in pipes eventually degrade the various piping components comprising the piping system necessitating their repair or replacement. Locations exposed to flow perturbations such as elbows, splitters, valves, reducers, connectors, etc. are especially prone to early failure.

In an attempt to extend the useful lives of these components, abrasion resistant coatings or liners are placed within their interiors. Typically elastomeric materials, such as polyurethane, rubber, and the like, these liner compositions are selected with an eye towards the entrained material. Corrosive flows must be matched with corrosion resistant materials, high and low temperature flows must be matched with temperature resistant materials, erosive flows must be matched with erosion resistant materials, and so on.

For example, in sandfill lines, the sand slurry plays havoc with the internals of the piping system. The slurry continuously flowing against the bend in an elbow will inexorably destroy the wall of the bend.

The most common method of determining whether an elbow or any conduit component is in danger of failing is manual inspection. Oftentimes a worker will visually and tactually inspect a fitting to see if it appears to be in danger of failure. However, the only realistic way to determine the internal status of the component is to remove and dismantle it. As can be appreciated this method is somewhat uncertain at best; is time consuming; and a cause of process inefficiency. Based upon experience, a component will be summarily dismantled or disposed of after a period of time whether or not the part is actually at risk. Of course, exceptions to the rule may cause physical injury and destruction of property.

Accordingly, there is a need for a simple, inexpensive monitoring device for determining the status of the liner of a conduit component.

SUMMARY OF THE INVENTION

There is provided an apparatus that includes sensors that are partially embedded in the interior of a conduit liner and are connected to the exterior of the conduit. An electrical plug communicates with the sensors and is receptive to a plug-in monitor that communicates the status of the liner.

PREFERRED EMBODIMENTS OF THE INVENTION

Figure 1:
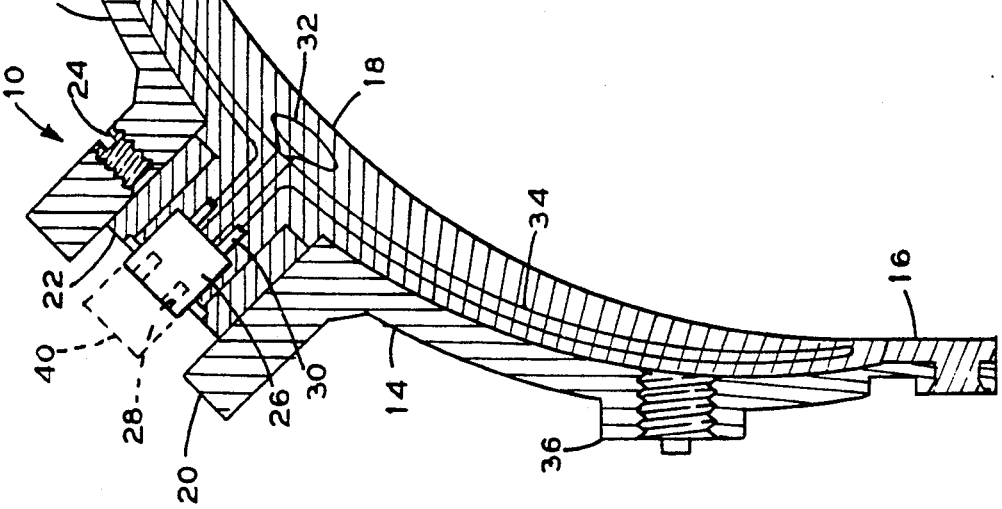
FIG. 1 is a cross-sectional view of an embodiment of the invention.

Referring to FIG. 1, there is shown a liner monitor 10 registered with a conduit 12. In this non-limiting example, a portion of an elbow 14 is shown. However, it should be understood that the generic word conduit includes any component associated with fluid conveyance—tubes, dividers, elbows, valves, joints, etc.

A suitable liner 16 is molded or otherwise attached to the interior of the conduit 12. From experience, the cross-section of the liner 16 is generally wider in the vicinity of the impact area 18 of an elbow 14 to compensate for erosive wear. The liner 16 is preferably made from polyurethane since it is easily moldable.

A cylindrical cavity 20 is oriented generally opposite the impact area 18. The cavity 20 accommodates a slidable cylindrical insert 22 that may be locked in position by at least one set screw 24. A multi-contact receptacle 26 having male and female contacts 30 and 28 is inserted into the insert 22. The receptacle 26 may be a four pin chassis mount socket Radio Shack TM Model No. 274-002.

In the embodiment shown, the male contacts 30 are electrically connected to an independent pair of wires 32 and 34 embedded in the liner 16. The wire 32 is preferably disposed adjacent to the impact area 18 and may be configured in a small closed loop such as a circle, oval, square, etc. The leads of the depicted arcuate wire 32 form the closed loop and are connected to two of the male contacts 30. The longitudinal wire 34 is elongated and extends over a wider area within the liner 16 than wire 32. The leads of the longitudinal wire 34 form a larger closed loop and are connected to two of the male contacts 30. The wires 32 and 34 form two separate circuits and except for a common source of electrical potential and ground are independent from one another.

Each female contact 28 in the receptacle 26 corresponds to a particular wire to maintain the integrity of the individual circuits.

Although two sets of wires 32 and 34 are shown, additional wires and contacts may be employed in various orientations within the liner 16.

For production purposes, the conduit 12 may be manufactured with the cavity 20 situated in the appropriate place to be monitored. The insert 22 and the receptacle 26 are inserted into the cavity 20, the set screw 24 tightened, and the wires 32 and 34 are connected to the male contacts 30. The wires 32 and 34 must have sufficient rigidity to maintain their orientation and their independence when the liner material 16 is injected into the conduit 12 and allowed to harden.

The liner material 16, typically polyurethane, is injected through access 36 which is then sealed.

After the liner 16 sets, the wires 32 and 34 are suspended in place. The lined conduit 12 is then installed in the piping system in the usual manner.

Figure 2:
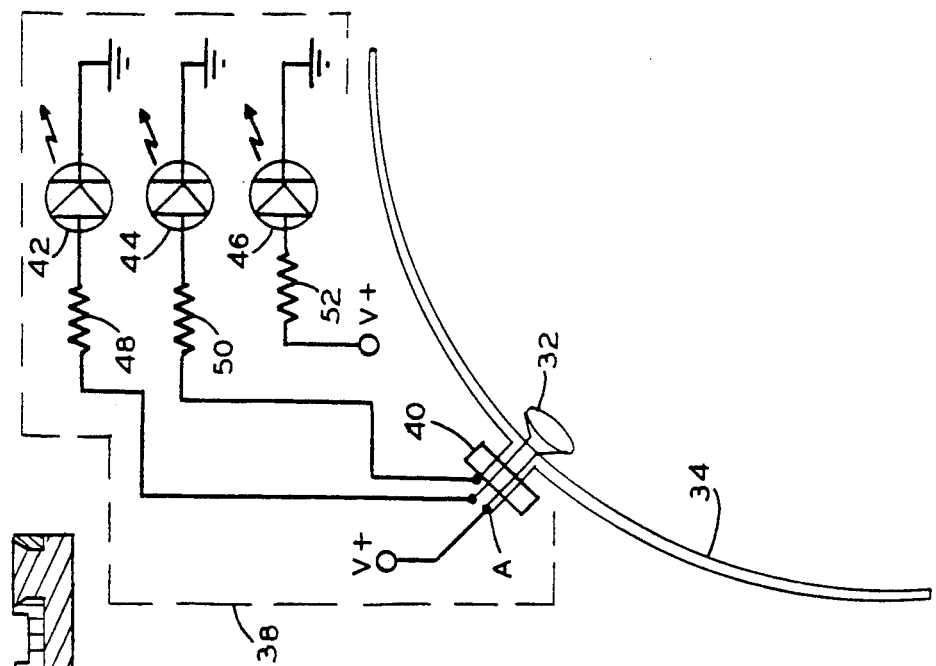
FIG. 2 is a schematic diagram of an alternative embodiment of the invention.

FIG. 2 depicts the circuitry of the monitor 10 in somewhat greater detail. A companion male plug 40 may be removably inserted into the receptacle 26. As will be appreciated shortly, the companion male plug 40 and the receptacle 26 may be keyed so that the same contacts are always matched when the companion male plug 40 is inserted into the receptacle 26.

Box 38 denotes a liner status circuit and power supply. Although the box 38 and its innards may be permanently hard wired to the conduit 12, it is envisioned that box 38 be mobile and hand-held.

The box 38 includes voltage source $V_+$, typically a 9 volt battery, and the plug 40. A plurality of light emitting diodes 42, 44 and 46 and associated resistors 48, 50 and 52 are connected to the common voltage source $V_+$ and ground.

The box 38, receptacle 26 or plug 40, may be configured so that one filament of wire 32 and wire 34 are ultimately ganged together at point A for the impression of $V_+$.

In order to determine the status of the liner 16, the male companion plug 40 is inserted into the receptacle 26. If the wires 32 and 34 are intact, continuous, and conductive; that is, the liner 16 has not yet been compromised because of erosion, chemical attack, temperature change, etc., all three LED's 42, 44 and 46 will light signifying a "good" status.

Over time, the entrained materials will begin to physically and chemically attack the liner 16. Initially, the destruction of the liner 16 is minimal and generally acceptable. The wires 32 and 34 are still continuous. Inexorably, however, the liner 16 will begin to fail exposing the wires 32 and 34. The wires 32 and 34 in turn will deteriorate under the continuous onslaught and eventually break interrupting the continuous circuit. At this point, the monitor 10 will indicate that the liner 16 has failed in the vicinity of the broken wire.

If, for example, only the LED's 42 and 46 are on, the wire 34 is broken. This indicates a warning condition and the liner 16 may have been breached. Similarly, if only the LED's 44 and 46 are on, the wire 32 is broken, again signifying a warning condition. If only the LED 46 remains on, both wires 32 and 34 are broken. This would signal that the liner 16 has been compromised in some fashion and a change of conduit 12 may be desirable.

If the plug 40 and the receptacle 26 are keyed and the LED's 42 and 44 are labelled, one will know immediately which wire is broken. This specific knowledge may be useful. However, if such detailed information is not necessary, the status of the conduit liner 16 still may be determined by simply counting the number of energized LED's. Moreover, the number of LED's is a function of the number of wires embedded in the liner 16.

The LED 46 serves as a test/on/off function. It may be switched (not shown) to conserve $V_+$.

Figure 3:
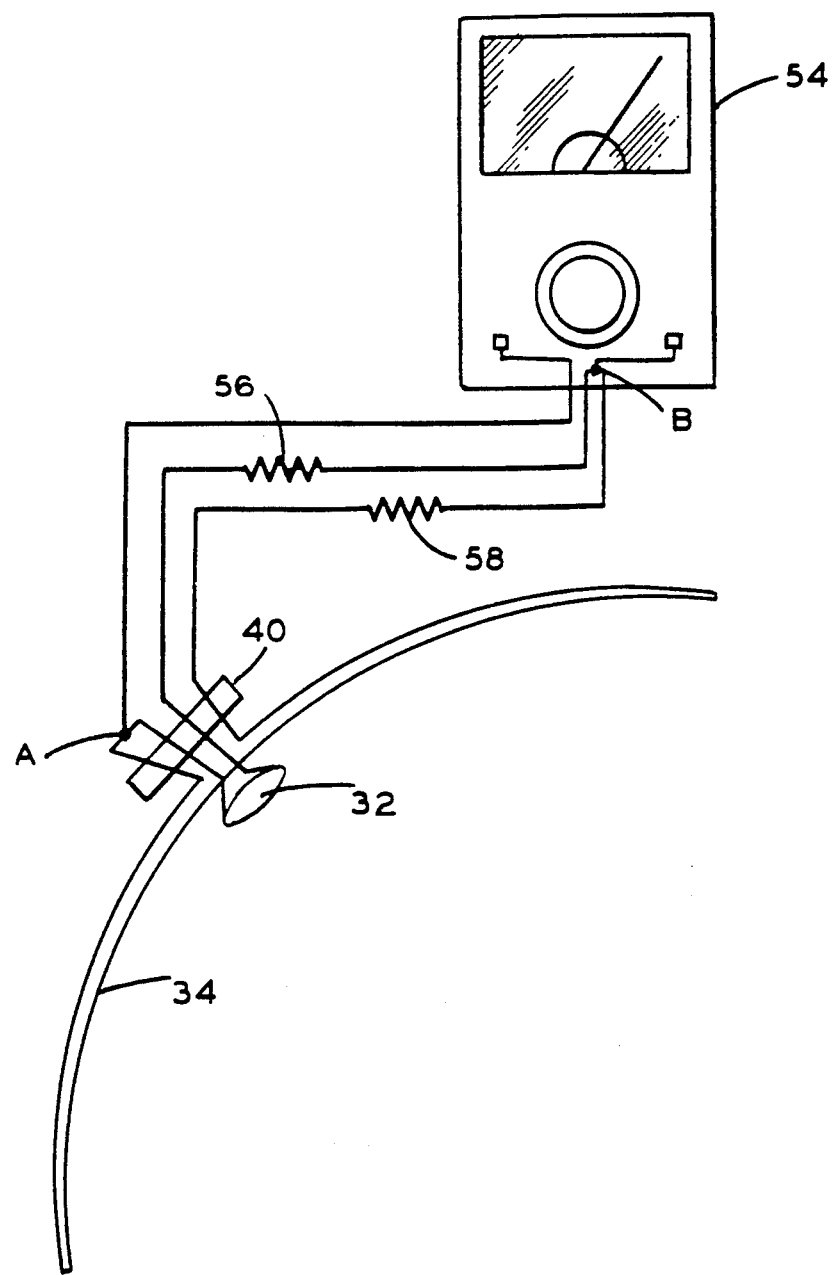
FIG. 3 is an alternative schematic embodiment of the invention.

FIG. 3 is an alternative embodiment of the liner monitor 10 employing a conventional volt-ohm test meter 54.

As before, the wires 32 and 34 share a common point A. The companion plug 40 is insertable into the receptacle 26. In this instance the leads also share a common point B. The two resistors 56 and 58 are in parallel with one another and are selected to deflect the meter 54 appropriately; say, 200 ohms for resistor 56 and 20 thousand ohms for resistor 58.

The resistors 56 and 58 are configured so that when the wires 32 and 34 are both intact, the cumulative resistance of the parallel circuits is low, allowing full deflection of the meter 54; thusly indicating a good status. Should one wire 32 or 34 be broken, the resistance is larger, therefore showing an intermediate reading. If both wires 32 and 34 are broken, the resistance is high and there will be little or no deflection of the meter 54 thereby indicating a potential failure condition. Permutations on the meter/resistor theme may be employed to similar advantage.

Figure 4:
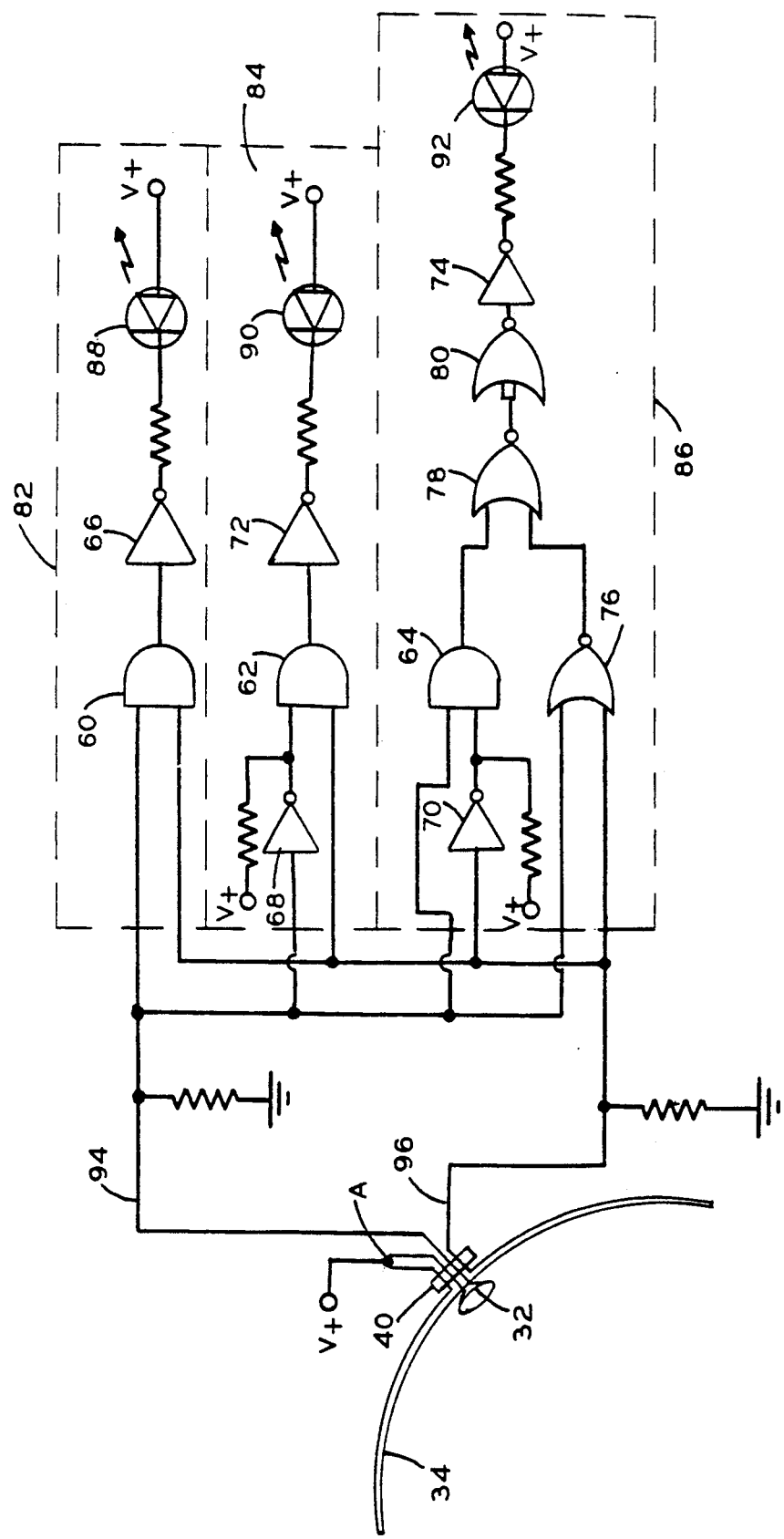
FIG. 4 is a schematic diagram of an alternative embodiment of the invention.

FIG. 4 depicts an alternative non-limiting warning scheme utilizing digital logic. The liner monitor 10 lends itself easily to various warning configurations.

The circuitry of FIG. 4 may be also hand-held or permanently installed.

The plug 40 includes leads 94 and 96 that are ultimately connected to AND gates 60, 62 and 64; inverters 66, 68, 70, 72 and 74; and NOR gates 76, 78 and 80. The resistors are selected accordingly.

Circuit sets 82, 84 and 86, divided up simply for non-limiting discussion purposes, terminate in LED's 88, 90 and 92.

The lead 94 is connected to the wire 32 and the lead 96 is connected to the wire 34. Point A is the common source of voltage $V_+$.

By observing the sequence of the LED's 88, 90 and 92, an operator can easily determine the status of the liner 16. The table below is a truth table for the circuit sets 82, 84, 86 and their associated LED's. By altering the configurations, the truth table may be changed. The LED's can be color coded, labelled, or both.

| Wire 32 | Wire 34 | LED 88 | LED 90 | LED 92 |
| --- | --- | --- | --- | --- |
| BAD | BAD | OFF | OFF | ON |
| BAD | OK | OFF | ON | OFF |
| OK | BAD | OFF | OFF | ON |
| OK | OK | ON | OFF | OFF |

While in accordance with the provisions of the statute, there is illustrated and described herein specific embodiments of the invention, those skilled in the art will understand that changes may be made in the form of the invention covered by the claims and that certain features of the invention may sometimes be used to advantage without a corresponding use of the other features.

The embodiments of the invention in which an exclusive property or privilege is claimed are defined as follows:

1. A conduit having an internal status indicator, the conduit comprising a wall, an interior liner adjacent to the wall, a cavity extending into the conduit, at least one deteriorative wire substantially embedded in the liner, the cavity adapted to accommodate a receptacle connected to the wire, and the receptacle adapted for association with an information display.

2. The conduit according to claim 1 wherein at least one wire forms a small closed circuit adjacent to the cavity within the liner.

3. The conduit according to claim 1 wherein at least one wire forms a closed longitudinal circuit within the liner.

4. The conduit according to claim 1 wherein at least two independent wires are disposed within the liner, the wires sharing a common source of electrical potential.

5. The conduit according to claim 1 wherein a keyed plug is inserted into the receptacle.

6. The conduit according to claim 1 wherein the information display includes liner condition indicators, the display communicating with the receptacle.

7. A system for determining the status of a conduit liner, the system comprising:
a) a conduit;
b) a liner disposed within the conduit;

c) at least one continuous deteriorative wire embedded within the liner;
d) at least one wire communicating with an externally connectable receptacle associated with a cavity extending into the conduit;
e) the receptacle adapted to communicate with a liner status display device; and
f) the wires communicating with external resistors configured in parallel circuitry, the resistors communicating with the liner status display device, and the liner status display device measuring and reporting the resistance of the parallel circuitry.

8. A system for determining the status of a conduit liner, the system comprising:

a) a conduit;
b) a liner disposed within the conduit;
c) at least one continuous deteriorative wire embedded within the liner;
d) at least one wire communicating with an externally connectable receptacle associated with a cavity extending into the conduit;
e) the receptacle adapted to communicate with a liner status display device;
f) the liner status display device adapted to sense and report the condition of the wire; and
g) the liner status display device including at least one light source, the light source adapted to indicate the condition of at least one wire.

* * * * *